(12) United States Patent
Burnett et al.

(10) Patent No.: US 9,194,847 B2
(45) Date of Patent: Nov. 24, 2015

(54) SAMPLE TRAY WITH MAGNETICALLY CLOSING DRAWER

(75) Inventors: Joshua A. Burnett, Taunton, MA (US);
James E. Usowicz, Webster, MA (US);
Daniel J. Gagne, Smithfield, RI (US);
Keith McGrath, Milford, MA (US);
Edwin Denecke, North Attleboro, MA (US)

(73) Assignee: Waters Technologies Corporation, Milford, MA (US)

(*) Notice: Subject to any disclaimer, the term of this patent is extended or adjusted under 35 U.S.C. 154(b) by 548 days.

(21) Appl. No.: 13/519,785

(22) PCT Filed: Jan. 11, 2011

(86) PCT No.: PCT/US2011/020749
§ 371 (c)(1),
(2), (4) Date: Aug. 22, 2012

(87) PCT Pub. No.: WO2011/085342
PCT Pub. Date: Jul. 14, 2011

(65) Prior Publication Data
US 2014/0079606 A1 Mar. 20, 2014

Related U.S. Application Data

(60) Provisional application No. 61/293,845, filed on Jan. 11, 2010.

(51) Int. Cl.
*B01L 99/00* (2010.01)
*G01N 30/24* (2006.01)
(Continued)

(52) U.S. Cl.
CPC ............... *G01N 30/24* (2013.01); *G01N 30/16* (2013.01); *G01N 30/20* (2013.01); *G01N 2035/00287* (2013.01); *G01N 2035/00346* (2013.01); *G01N 2035/0498* (2013.01)

(58) Field of Classification Search
CPC ..... B01L 2300/04; B01L 99/00; A47B 81/00; G01N 30/02
USPC ........ 73/61.52–61.59; 422/70, 560–562, 565; 206/557–561; 312/333
See application file for complete search history.

(56) References Cited

U.S. PATENT DOCUMENTS 4,027,934 A 6/1977 Wiser
4,678,081 A 7/1987 Richter
(Continued)

FOREIGN PATENT DOCUMENTS

EP 0902271 A2 3/1999
FR 2788042 A1 7/2000
(Continued)

OTHER PUBLICATIONS

Machine translation KR20-0442123, downloaded Apr. 5, 2015.*
(Continued)

*Primary Examiner* — Jan Ludlow
(74) *Attorney, Agent, or Firm* — Schmeiser, Olsen & Watts LLP (57) ABSTRACT

A sample manager of a liquid chromatography system uses a sample tray having a base with side walls separated by a cross wall that divides the base into two compartments. The side walls and cross wall bound each compartment on three sides. A fourth side of each compartment is open. Each compartment is sized to closely receive a sample-vial carrier. Each compartment has a magnet affixed to a bottom surface at an edge of the open fourth side. Each of two drawers slides into the open fourth side of one compartment. Each drawer has a support surface with a magnet affixed at an edge of its bottom side, which aligns with the magnet affixed to the bottom surface of the compartment. The magnet of the drawer and the magnet of the compartment bias the drawer into its compartment when the magnets are brought into proximity of each other.

12 Claims, 12 Drawing Sheets

(51) Int. Cl.
  *G01N 30/16*  (2006.01)
  *G01N 35/00*  (2006.01)
  *G01N 30/20*  (2006.01)
  *G01N 35/04*  (2006.01)

(56) References Cited

U.S. PATENT DOCUMENTS

| | | |
|---|---|---|
| 5,483,843 A | 1/1996 | Miller et al. |
| 5,900,557 A | 5/1999 | Tanihata et al. |
| 7,329,393 B2 | 2/2008 | Backes et al. |
| 7,390,390 B2 | 6/2008 | Yamamoto et al. |
| 2008/0172023 A1 | 7/2008 | Thompson et al. |
| 2014/0286124 A1* | 9/2014 | Donohue et al. ............ 366/342 |

FOREIGN PATENT DOCUMENTS

| | | | |
|---|---|---|---|
| KR | 20-0442123 | * | 10/2008 |
| KR | 20-0442123 Y1 | | 10/2008 |

OTHER PUBLICATIONS

Extended European Search Report in related European Patent Application No. 11732295.8, mailed on May 28, 2014; 7 pages.

International Search Report and Written Opinion in counterpart international application No. PCT/US2011/02749 dated Mar. 7, 2011; 8 pages.

* cited by examiner

SAMPLE TRAY WITH MAGNETICALLY CLOSING DRAWER

RELATED APPLICATION

This application claims priority to and the benefit of U.S. provisional application Ser. No. 61/293,845, filed on Jan. 11, 2010, the entirety of which application is incorporated by reference herein.

FIELD OF THE INVENTION

The invention relates generally to liquid chromatography systems. More specifically, the invention relates to sample trays used in a sample manager of a liquid chromatography system.

BACKGROUND

Chromatography is a set of techniques for separating a mixture into its constituents. For instance, in a liquid chromatography application, a pump takes in and delivers a mixture of liquid solvents to a sample manager, where an injected sample awaits its arrival. In an isocratic chromatography application, the composition of the liquid solvents remains unchanged, whereas in a gradient chromatography application, the solvent composition varies over time. The mobile phase, comprised of a sample dissolved in a mixture of solvents, passes to a column, referred to as the stationary phase. By passing the mixture through the column, the various components in the sample separate from each other at different rates and thus elute from the column at different times. A detector receives the elution from the column and produces an output from which the identity and quantity of the analytes may be determined.

SUMMARY

In one aspect, the invention features a sample tray for use in a sample manager of a liquid chromatography system. The sample tray comprises a base with opposing spaced-apart side walls separated by a cross wall that divides the base into two compartments, with one compartment on each side of the cross wall. The side walls and cross wall bound each of the two compartments on three sides, with a fourth side of each compartment being open. Each compartment is sized to closely receive a sample-vial carrier. Each compartment has a surface with a magnet affixed to an underside of the surface at an edge of the open fourth side of that compartment.

A pair of drawers is slidably coupled to the base. Each drawer slides into the open fourth side of one of the two compartments over the surface of that compartment. Each drawer has a support surface for supporting a sample-vial carrier. The support surface has a top side and a bottom side. The support surface of each drawer has a magnet affixed on the bottom side. The magnet on the bottom side of the support surface of each drawer is in alignment with the magnet affixed to the bottom surface of the compartment into which that drawer slides. The magnet of each drawer and the magnet of the compartment into which that drawer slides bias that drawer into its compartment when the magnets are brought into proximity of each other.

In another aspect, the invention features a sample tray for use in a sample manager of a liquid chromatography system. The sample tray includes a with opposing spaced-apart side walls separated by a back wall. The side walls and back wall bound a compartment on three sides, with a fourth side of the compartment being open. The compartment is sized to closely receive a sample-vial carrier. The compartment has a top surface and a bottom surface with a magnet affixed to the bottom surface at an edge of the open fourth side of that compartment.

A drawer is slidably coupled to the base for sliding into the compartment through the open fourth side. The drawer has a support surface for closely receiving a sample-vial carrier. The support surface has a top side and a bottom side. The support surface of the drawer has a magnet affixed on the bottom side. The magnet on the bottom side of the support surface is in alignment with the magnet affixed to the bottom surface of the compartment along a path taken by the drawer when sliding into the compartment. The magnets bias the drawer into compartment when brought into proximity of each other.

In still other aspects, the invention features a liquid chromatography system and a sample manager comprising a thermal chamber and a sample tray mounted within the thermal chamber. The sample tray comprises a base having opposing spaced-apart side walls separated by a cross wall that divides the base into two compartments, with one compartment on each side of the cross wall. The side walls and cross wall bound each of the two compartments on three sides, with a fourth side of each compartment being open. Each compartment is sized to closely receive a sample-vial carrier. Each compartment has a top surface and a bottom surface with a magnet affixed to the bottom surface at an edge of the open fourth side of that compartment.

A pair of drawers is slidably coupled to the base. Each drawer sliding into the open fourth side of one of the two compartments. Each drawer has a support surface for supporting a sample-vial carrier. The support surface has a top side and a bottom side. The support surface of each drawer has a magnet affixed at an edge of the bottom side. The magnet at the edge of the bottom side of the support surface of each drawer is in alignment with the magnet affixed to the bottom surface of the compartment into which that drawer slides. The magnet of each drawer and the magnet of the compartment into which that drawer slides biasing that drawer into its compartment when the magnets are brought into proximity of each other.

BRIEF DESCRIPTION OF THE DRAWINGS

The above and further advantages of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

DETAILED DESCRIPTION

When performing a liquid chromatographic run, a technician loads an array of vials containing samples onto a carrier, places the sample-vial carrier onto a drawer of a sample tray, and slides the drawer into its compartment. As described herein, the sample tray employs magnets to lock the drawer into its compartment; the drawer and the compartment both have a magnet. As the drawer slides into its compartment, the magnets approach each other, and the strength of their magnetic attraction increases. When they are close proximity to each other, the magnets pull the drawer against the compartment with a tactile snapping sensation, thereby providing a positive confirmation to the technician that the drawer has fully closed. One embodiment of a sample tray has two compartments separated by a center wall. The center of the sample tray is coupled to a rotary drive mechanism for rotational movement within the sample chamber of the sample manager.

Figure 1:
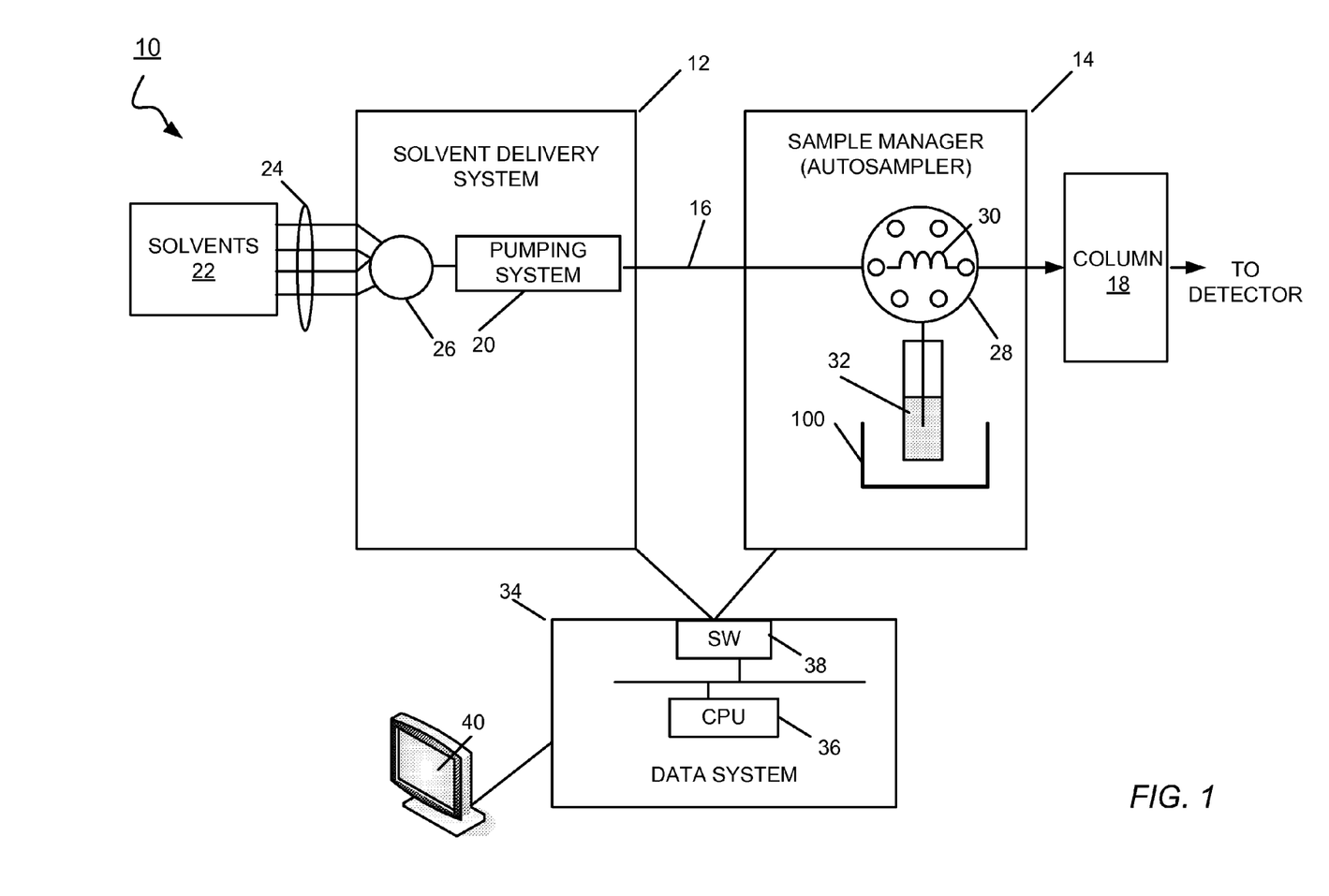
FIG. 1 is a functional block diagram of an embodiment of a liquid chromatography system.

FIG. 1 shows an embodiment of a liquid chromatography system 10 for separating a mixture into its constituents. The liquid chromatography system 10 includes a solvent delivery system 12 in fluidic communication with a sample manager 14 (also called an injector or an autosampler) through tubing 16. The sample manager 14 is in fluidic communication with a chromatographic column 18. A detector (not shown), for example, a mass spectrometer, is in fluidic communication with the column 18 to receive the elution.

The solvent delivery system 12 includes a pumping system 20 in fluidic communication with solvent reservoirs 22 from which the pumping system 20 draws solvents (liquid) through tubing 24. In one embodiment, the pumping system 20 is embodied by a low-pressure mixing gradient pumping system having two pumps fluidically connected in series. In the low-pressure gradient pumping system, the mixing of solvents occurs before the pump, and the solvent delivery system 12 has a mixer 26 in fluidic communication with the solvent reservoirs 22 to receive various solvents in metered proportions. This mixing of solvents occurs in accordance with an intake profile, and produces a solvent (mobile phase) composition that varies over time (i.e., the gradient).

The pumping system 20 is in fluidic communication with the mixer 26 to draw a continuous flow of gradient therefrom for delivery to the sample manager 14. Examples of pumping systems that can be used to implement the pumping system 20 include, but are not limited to, the 2545 Quaternary Gradient Module and the 2555 Quaternary Gradient Module, manufactured by Waters Corp. of Milford, Mass.

The sample manager 14 includes an injector valve 28 having a sample loop 30. The sample manager 14 operates in one of two states: a load state and an injection state. In the load state, the position of the injector valve 28 is such that the sample manager 14 loads the sample 32 into the sample loop 30. The sample 32 is drawn from a vial contained by a sample-vial carrier. The sample-vial carrier sits on a sample tray 100 within a thermal chamber of the sample manager 14. In the injection state, the position of the injector valve 28 changes so that sample manager 14 introduces the sample in the sample loop 30 into the continuously flowing mobile phase from the solvent delivery system. The mobile phase thus carries the sample into the column 18.

The liquid chromatography system 10 further includes a data system 34 that is in signal communication with the solvent delivery system 12 and the sample manager 14. The data system 34 has a processor 36 and a switch 38 (e.g., an Ethernet switch) for handling signal communication between the solvent delivery system 12 and sample manager 14, as described herein. Signal communication among the various systems and instruments can be electrical or optical, using wireless or wired transmission. A host computing system 40 is in communication with the data system 34 by which a technician can download various parameters and profiles (e.g., an intake velocity profile) to the data system 34.

Figure 2:
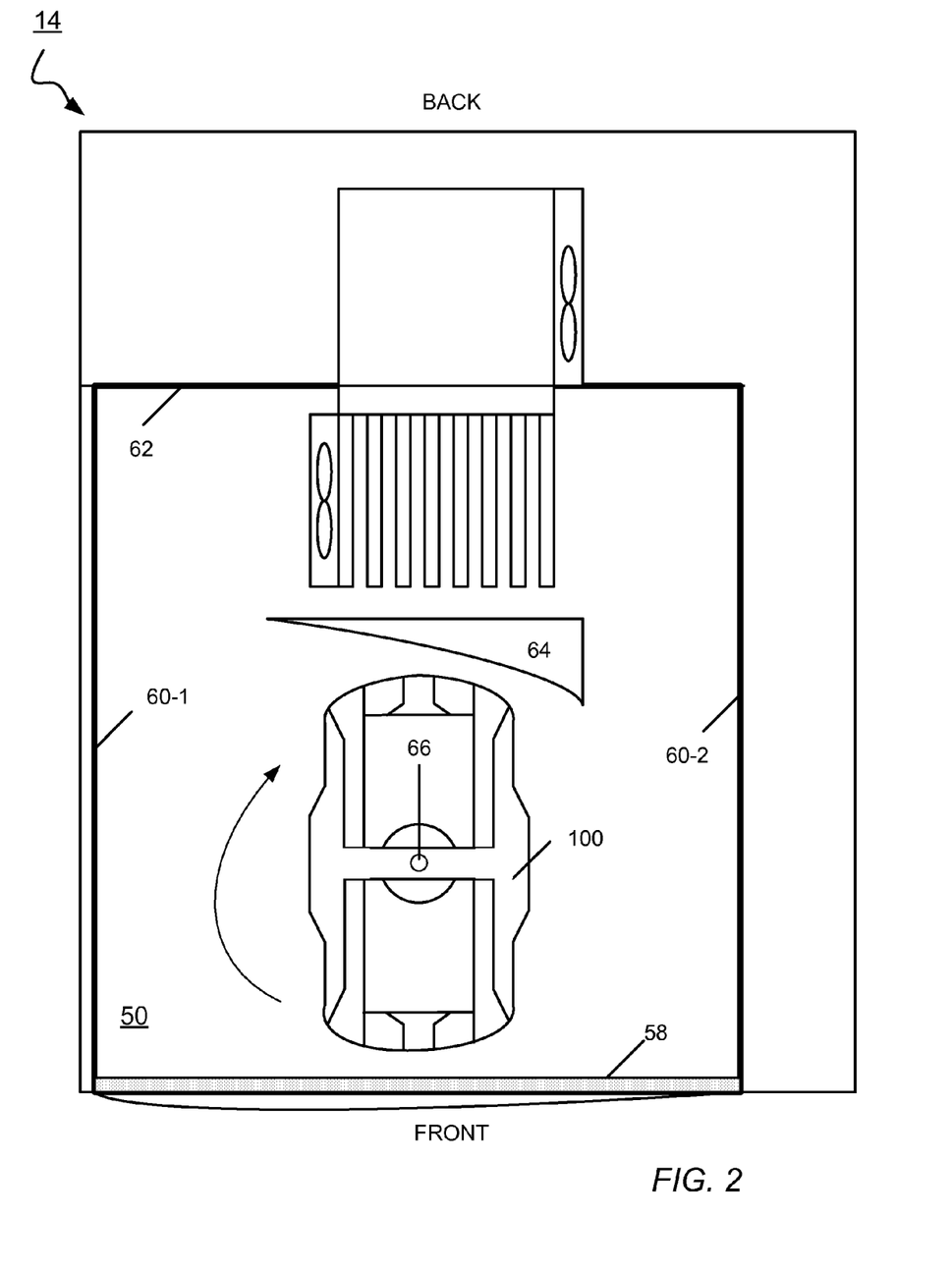
FIG. 2 is a top view of an embodiment of a sample manager.

FIG. 2 shows top view of an embodiment of the sample manager 14 including a sample chamber 50 having a front wall 56 with a door 58, side walls 60-1, 60-2, and a back wall 62. Within the sample chamber 50 is an interior wall 64 used to form an air duct along the back wall 62 and a two-compartment sample tray 100 coupled to a rotary drive mechanism (not shown, being beneath the sample tray and a datum plate) for rotational movement about a pivot point 66. In general, a technician inserts or removes a sample-vial carrier from the compartment that is the closer of the two to the door 58.

Figure 3:
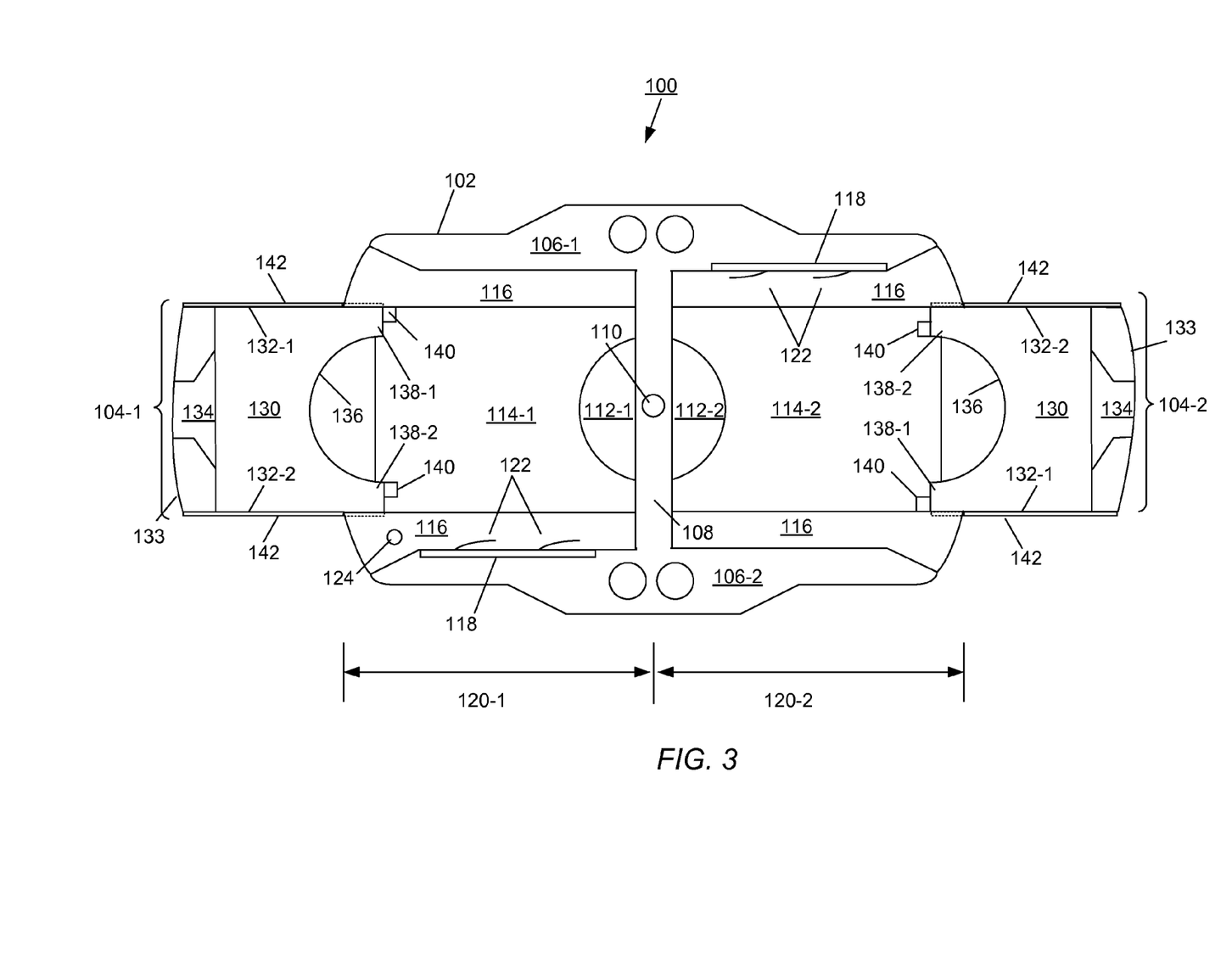
FIG. 3 is a top view of an embodiment of a sample tray having a pair of magnetically closing drawers.

FIG. 3 shows a top view of an embodiment of the sample tray 100 having a base 102 and a pair of magnetically closing drawers 104-1, 104-2 (generally, 104). As shown, the drawers 104 are fully open, which is their preferred orientation for placing a sample vial carrier onto a drawer. The base 102 has opposing side walls 106-1, 106-2 (generally, 106) and a cross wall 108 bisecting each side wall 106. The side walls 106 and cross wall 108 are of uniform height and, when viewed from above, together form the capital letter H, with the cross-wall 108 dividing the sample tray 100 into two compartments 120-1, 120-2 (generally, 120). The two compartments 120 are symmetrically inverted, like the two halves of a playing card. Each compartment can hold a rectangular 3.5"×5" sample-vial carrier. In one embodiment, the compartments are approximately 5" wide by 3.5" deep. Alternatively, the compartments can be 3.5" wide by 5" deep (provided the sample chamber is large enough for this length of sample tray). Compartments can also be designed to support sample-vial carriers of different dimensions without departing from the principles of the invention.

Midway in the cross wall 108 is a circular opening 110 for receiving a bolt or a post by which to secure the sample tray 100 to a rotary drive mechanism disposed below the sample chamber. On each of the opposite sides of the cross wall 108 is a semicircular platform 112-1, 112-2 (generally, 112). The semicircular platforms 112 rise above sunken surfaces 114-1, 114-2 (generally, 114) of the base 102. The two semicircular platforms 112 are opposite halves of a circular platform bisected by the cross wall. This circular platform and the circular opening 110 in the cross wall are concentric.

Along each side wall 106, on both sides of the cross wall 108, is a platform 116 raised above the plane of the depressed surfaces 114. Each side wall 106-1, 106-2 has an indent 118 and, within that indent, a pair of metallic leaf springs 122 extending laterally from the side wall. The leaf springs 122 are catty-cornered across the sample tray.

The sample tray has one calibration hole 124, which is located in one of the side platforms 116. The calibration hole 124 is an exception to the inverted symmetry between the tray compartments 120, there being only one such hole for the sample tray. In this embodiment, the calibration hole 124 is in the compartment 120-1 of the sample tray and penetrates entirely through the side platform 116 along side wall 106-2. With the sample tray mounted within the sample chamber, a technician aligns the calibration hole 124 with a hole in the datum plate. A metallic pin is inserted through the calibration hole and datum plate hole. During calibration, an encoder detects this pin and uses it to establish a home (i.e. reference) position from which all other tray positions are known. The pin is removed after calibration.

Each drawer 104 has a planar surface 130 with opposing side edges 132-1, 132-2 (generally 132), a handle 134 at a front edge 133, and an arcuate rear edge 136 that form prongs 138-1, 138-2 (generally, 138). Rising at the end of each prong 138 is an arching post 140. The posts 140 serve as positional guides or locators for directing a sample-vial carrier onto the planar surface 130. Each side edge 132 has a tongue 142 extending along a length of that edge. The tongues 142 closely enter grooves (FIG. 9) in the sides of opposite side platforms 116. As a drawer slides into its compartment, the tongues 142 of the drawer slide through the grooves in the side platforms 116.

Figure 4:
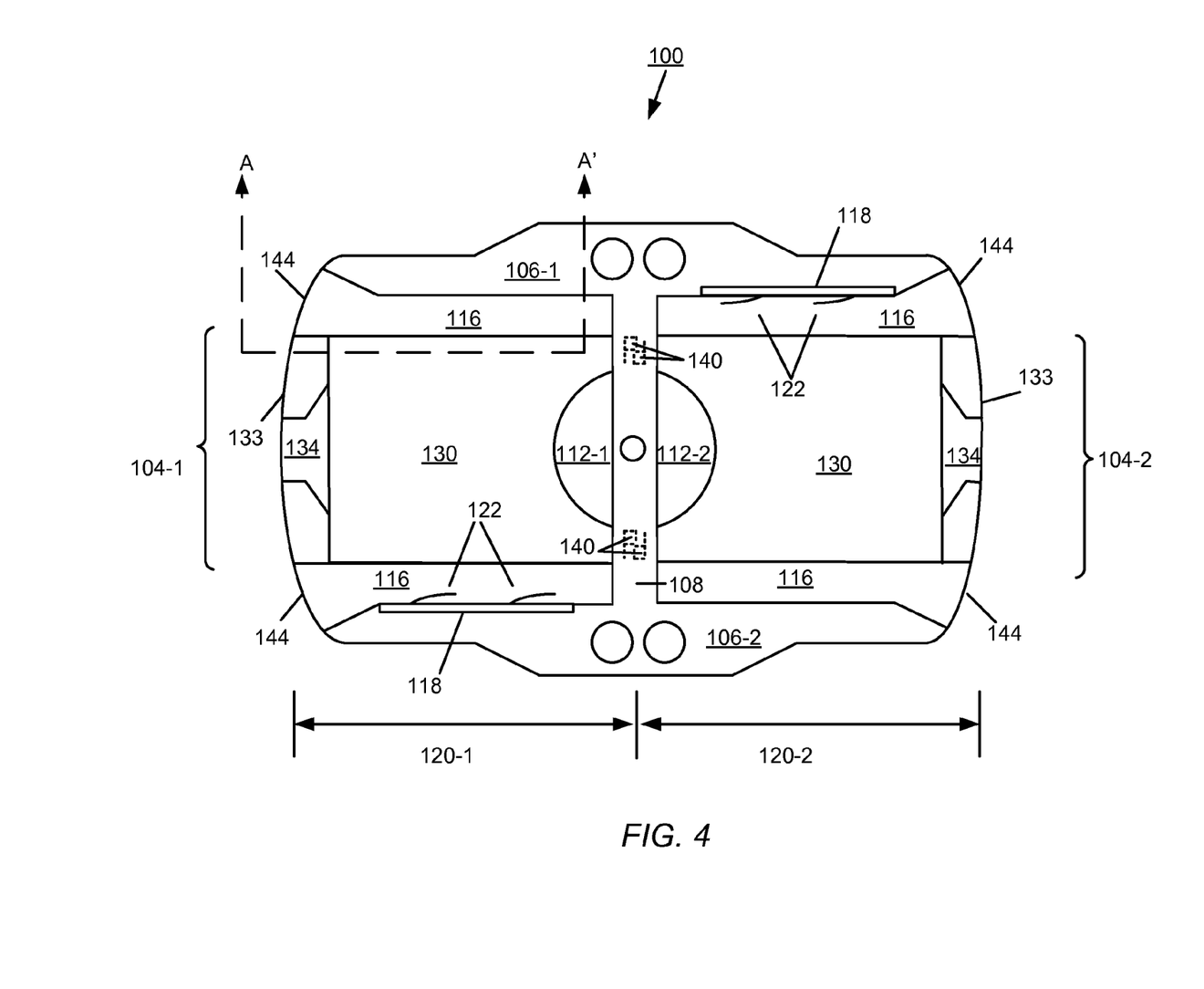
FIG. 4 is a top view of an embodiment of the sample tray having a pair of magnetically closing drawers in the closed position.

FIG. 4 shows a top view of the sample tray 100 with the drawers 104-1, 104-2 fully inserted into their respective compartment 120-1, 120-2. With the drawer in its compartment, the planar surface 130 of each drawer fits closely between a pair of opposing side platforms 116. The rear arcuate edge 136 of the drawer closely abuts the semicircular platform 112, like matching pieces of a puzzle. The arching posts 140 and tips of the prongs 138 pass through openings (FIG. 10) in the side of the cross wall 108 and stop within close proximity of their counterpart arching posts 140 of the other drawer. The front edge 133 of the drawer forms a smooth, continuous curve with the front edges 144 of the side platforms 116. The planar surface 130 of the drawer, the semicircular platform 112, and side platforms 116 are approximately of uniform height to provide a planar surface upon which to hold level a sample-vial carrier. The pair of leaf springs 122 extending from one side wall 106 operates to bias such a sample-vial carrier sitting within the drawer towards the side wall 106 on the opposite side.

Figure 5:
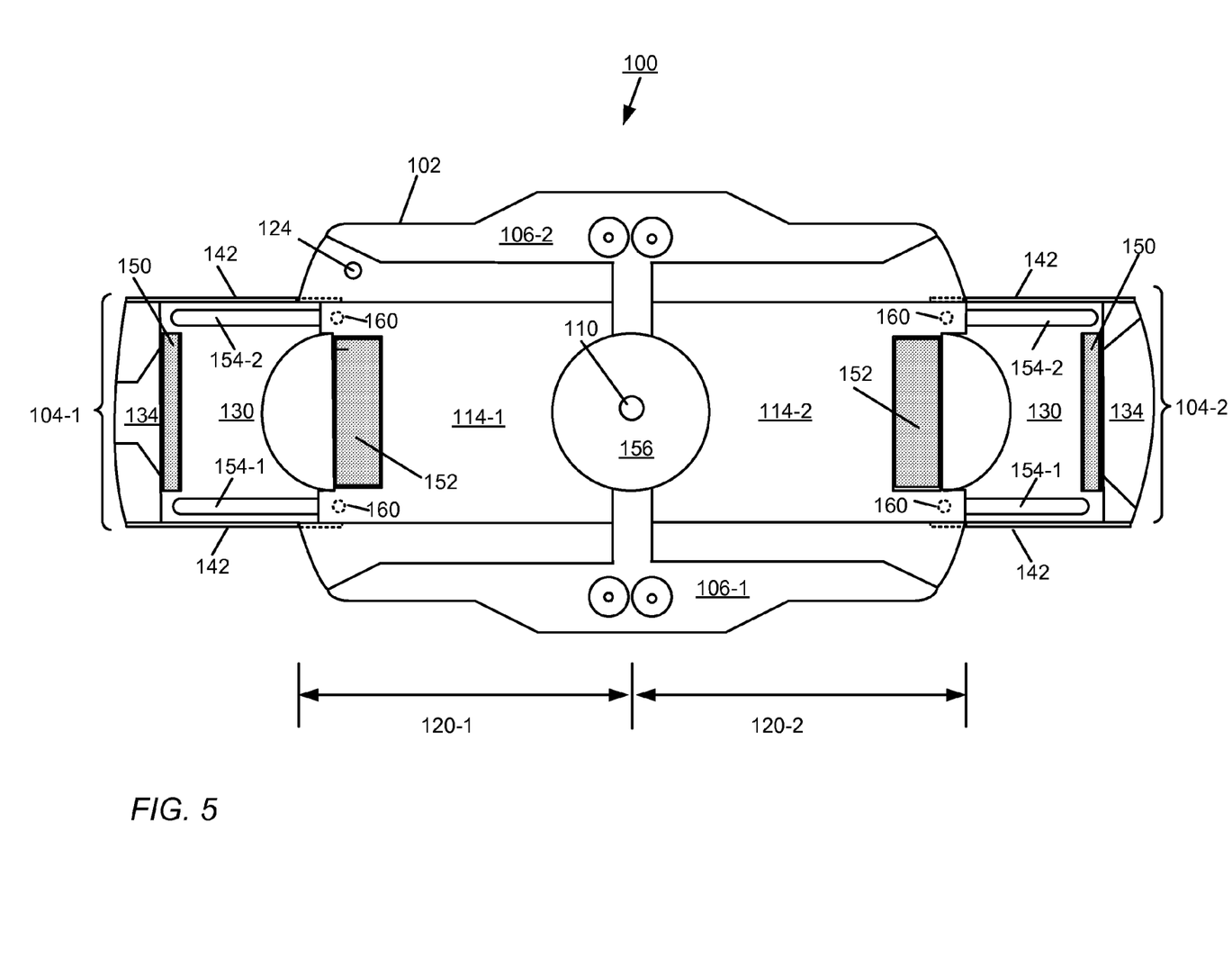
FIG. 5 is a bottom view of the sample tray with the drawers in the open position.

FIG. 5 shows a bottom view of the sample tray 100 with its drawers 104-1, 104-2 fully extended. Affixed to the underside of each drawer 104, near the handle 134, is a permanent bar magnet 150. Another permanent bar magnet 152 is affixed on the underside of the sunken surface 114 of each compartment 120. The magnets 150, 152 are oriented to attract each other as the drawer slides into its compartment 120. When the magnets 150, 152 come into range of their magnetic pull, the attractive magnetic force snaps the drawer within and against its compartment 120, giving the technician a tactile sensation that the drawer is fully closed. When the drawer is fully within its compartment, the edges of the magnets 150, 152 abut each other. In one embodiment, the length, thickness, and width of the bar magnet 150 affixed to the drawer are 2"×0.125"×0.2", respectively, and those of the bar magnet 152 affixed to the sunken surface 114 are 2"×0.125"×0.5", respectively.

The underside of each drawer 104 has a pair of tracks 154-1, 154-2 (generally, 154). Each track 154 receives a raised circular nub 160 that projects slightly from the topside of the surface 114. The nubs 160 slide within the tracks as the drawer slides in and out over the sunken surface 114 of the base 102. In addition, the raised nubs 160 keep the drawers 104 from detaching from the base.

Directly beneath the semicircular platforms 112 on the top side of the sample tray is a corresponding circular region 156. The circumference of the circular region 156 rises above the plane of the surrounding surfaces 114-1, 114-2; the interior of the circular region 156 lies below the plane. This raised circumference and depressed interior serve to position the sample tray upon a circular dais within the base of the sample chamber 50. The sample tray is coupled to this circular dais (via the hole 110).

Figure 6:
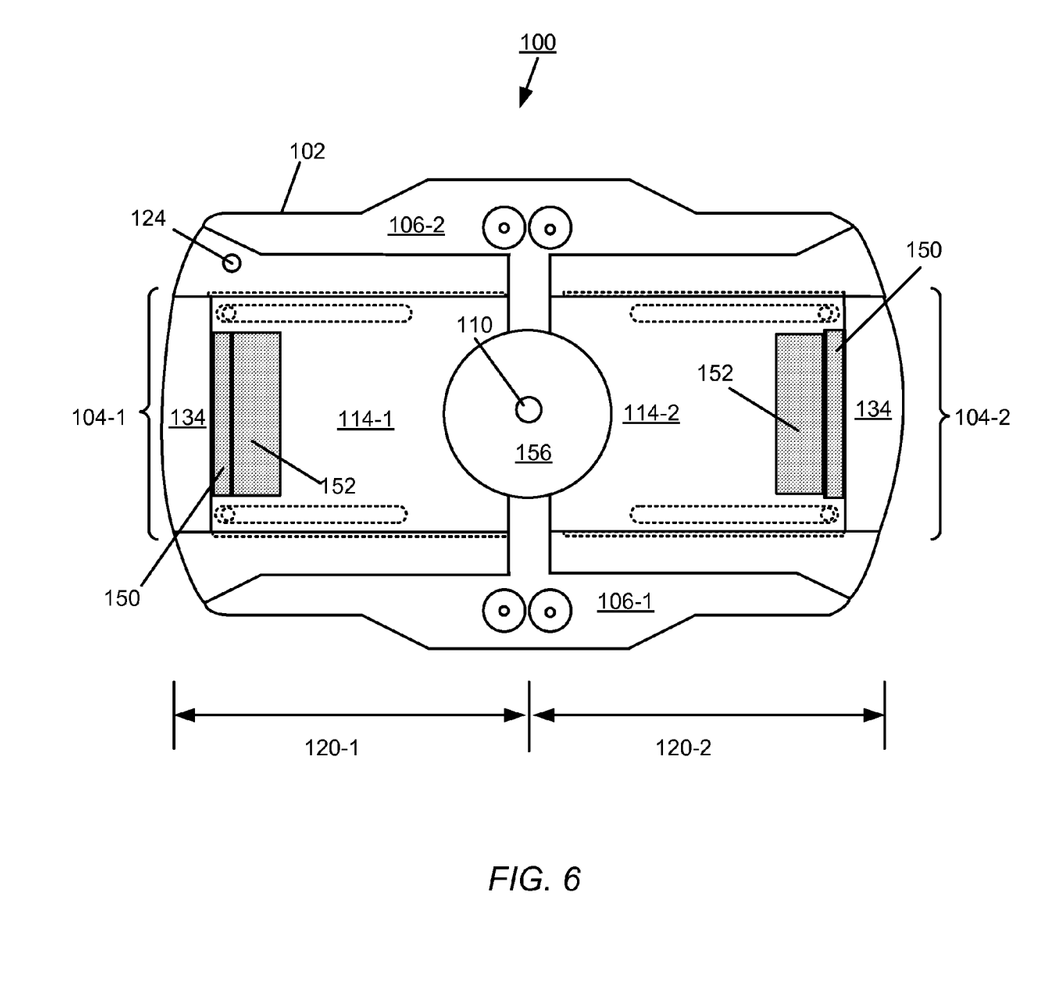
FIG. 6 is a bottom view of the sample tray with the drawers in the closed position.

FIG. 6 shows a bottom view of the sample tray with the drawers 104 fully closed. In the closed position, an edge of the bar magnet 150 on the underside of the drawer abuts an edge of the bar magnet 152 on the underside of the base surface 114. The attraction between the magnets 150, 152 is strong enough to keep the drawer secured in the closed position during rotation of the tray, yet sufficiently weak to permit a technician to pull the drawer out of its compartment. Because of permissible tolerances, some sample-vial carriers may have a depth that is slightly larger than the depth of the drawer, thus preventing the drawer from fully closing, that is, the magnets 150, 152 are unable to abut. Notwithstanding, the attractive force of the magnets is still sufficient to hold the drawer firmly in its compartment 120.

The combined biasing of the leaf springs 122 and the magnets 150, 152 operates to urge the A-1 position of the sample vial carrier within the drawer towards the left-side interior corner of the compartment 120.

Figures 7, 8:
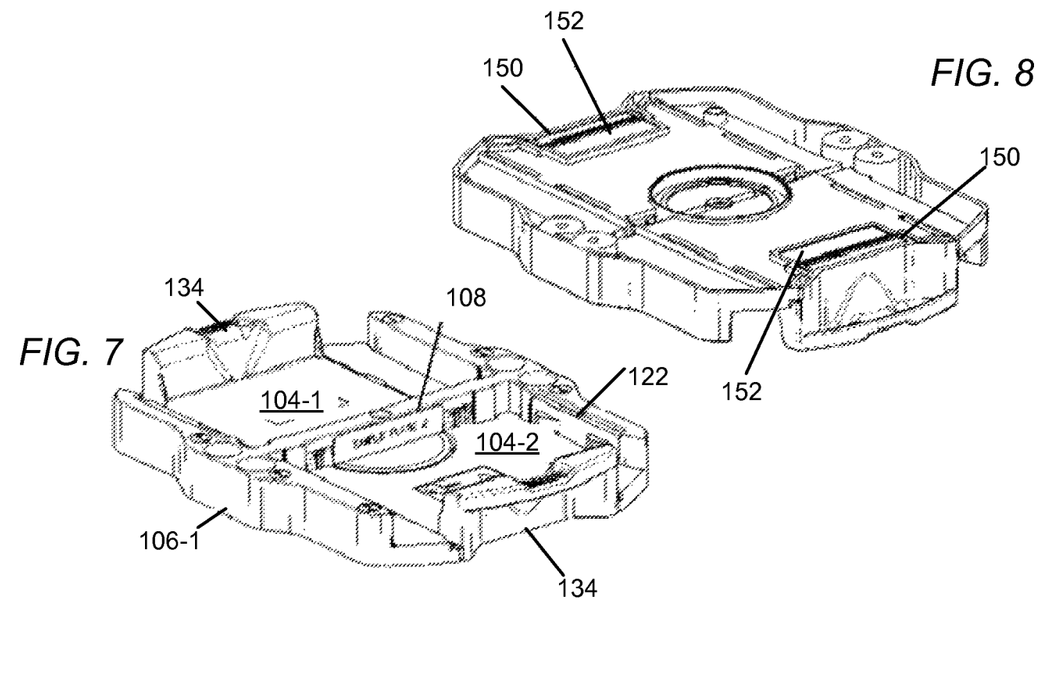
FIG. 7 is an isometric view of the sample tray with the drawers in the open position.
FIG. 8 is an isometric view of the sample tray with the drawers in the closed position.

FIG. 7 shows an isometric top view of the sample tray 100, showing the drawers 104, including their handles 134 and leaf springs 122, in detail. FIG. 8 shows an isometric bottom view of the sample tray 100 with the magnets 150, 152 securing the drawers 104 in their closed positions.

Figure 9:
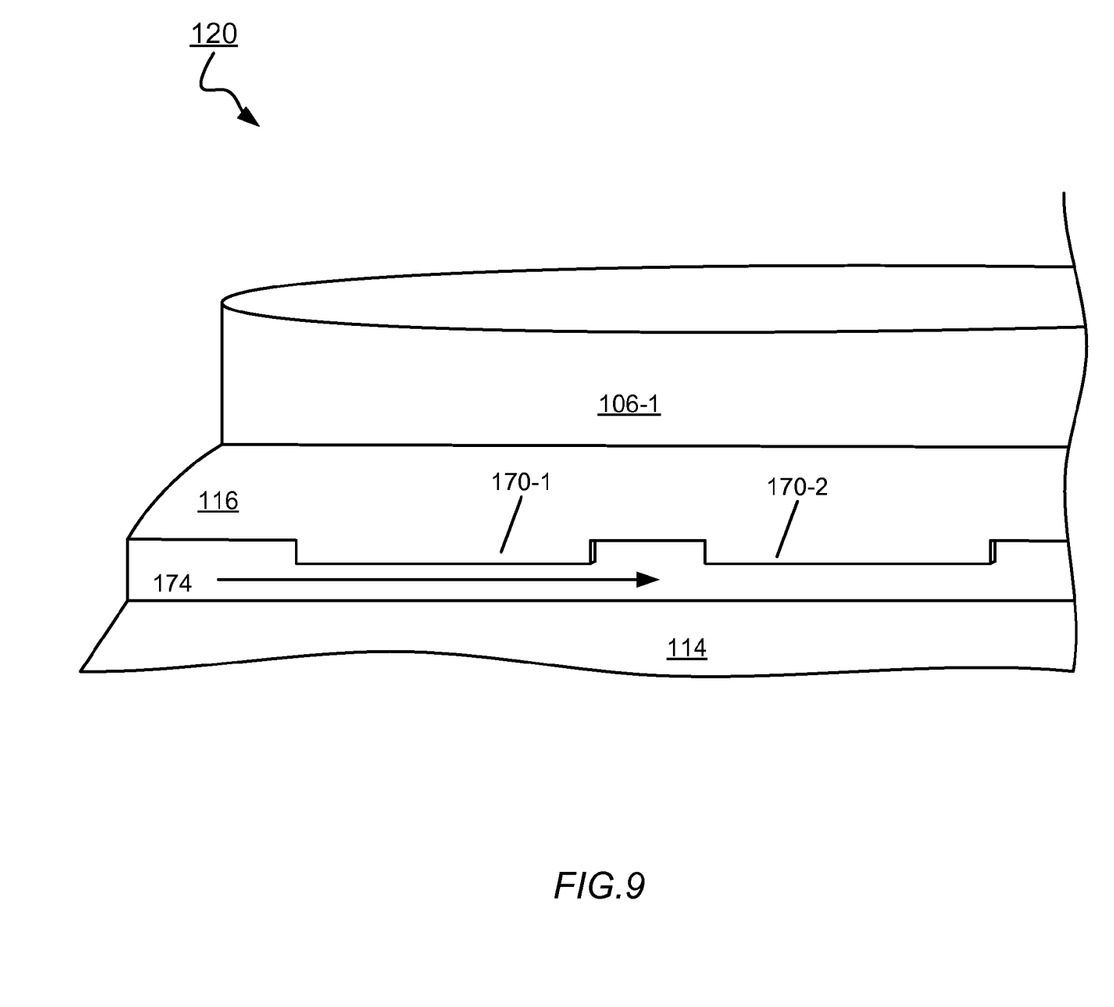
FIG. 9 is a side view of a compartment of the sample tray.

FIG. 9 shows a cross section of one side of a compartment 120 taken along line A-A' in FIG. 4 (with the drawer 104-1 removed). The view shows the side wall 106-1, the side platform 116 along the bottom of the side wall 106-1, and a pair of overhanging lips 170-1, 170-2 (generally, 170). The lips 170 overhang the sunken surface 114; together, the lips 170 and surface 114 form a side groove 174 through which the tongue 142 (FIG. 5) slides as the drawer is moved in and out.

Figure 10:
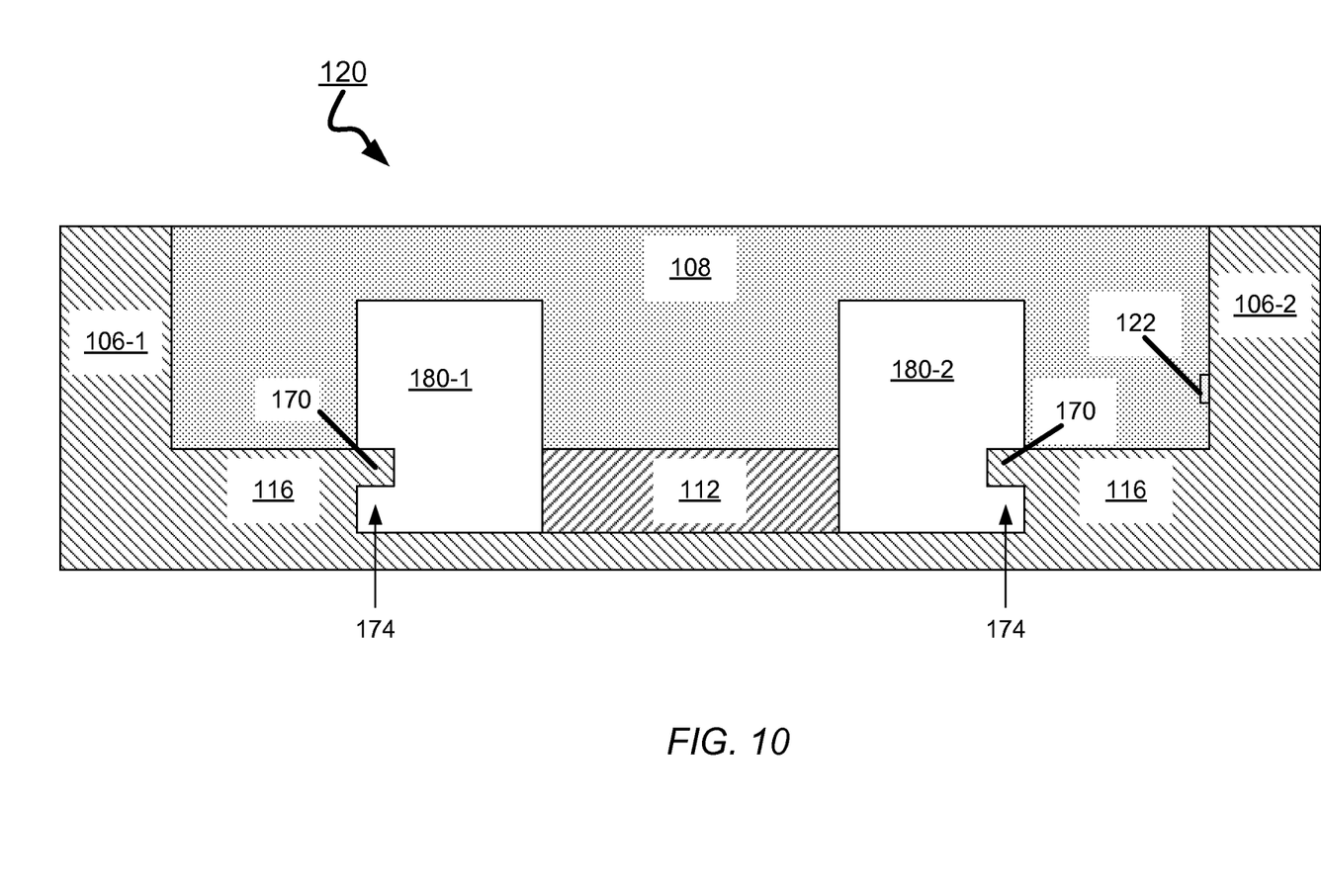
FIG. 10 is a front view of a compartment of the sample tray.

FIG. 10 shows a front view of one compartment 120 of the sample tray, showing the side walls 106-1, 106-2 separated by the cross-wall 108. The cross wall has a pair of openings 180-1, 180-2 (generally, 180) into which the arching posts 140 and tips of the prongs 138 of a drawer enter when a drawer is fully closed. Extending from each side wall 106 is a side platform 116, and extending from each side platform 116 are the overhanging lips 170. The open ends of the side grooves 174 are below the overhanging lips 170. At the bottom of the cross wall 108, between the openings 180, is the semicircular platform 112. Projecting from a surface of the side wall 106-2 is a leaf spring 122 (end view).

Figure 11:
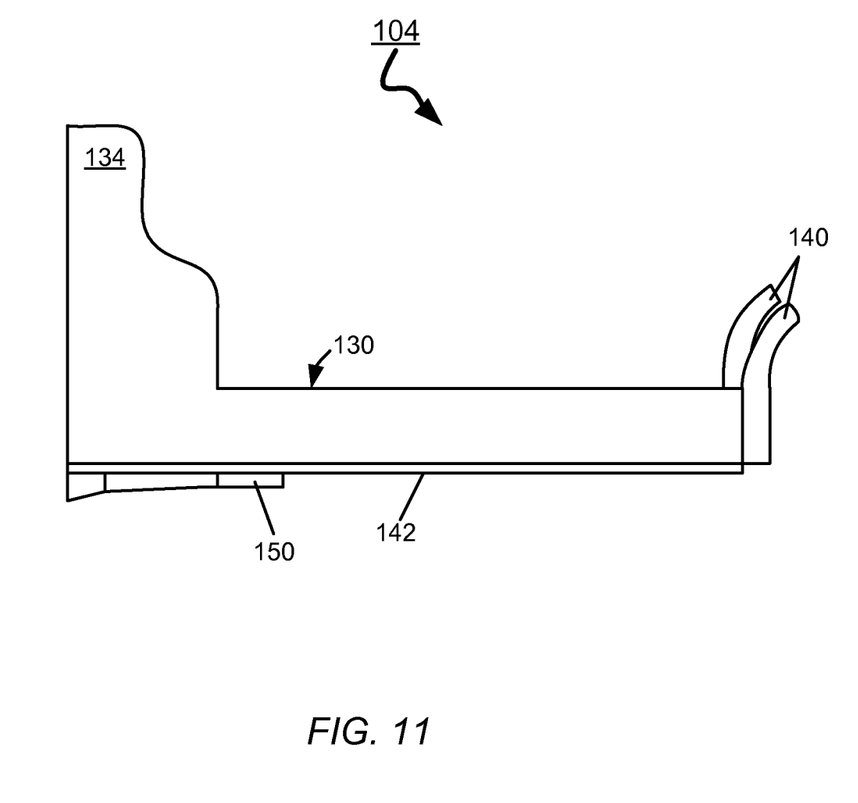
FIG. 11 is a side view of a drawer.

FIG. 11 shows a side view of a drawer 104. At a front end of the drawer is the handle 134. The center of the handle is ergonomically shaped to be grasped comfortably between the distal phalange of a person's forefinger and the person's thumb (for pushing and pulling the drawer in and out from the compartment). Affixed to the underside of the drawer, below the handle 134, is the bar magnet 150. At the opposite end of the support surface 130 are the arching posts 140, which bend at their tips away from the drawer. Along a lower edge of the drawer is a tongue 142.

Figure 12:
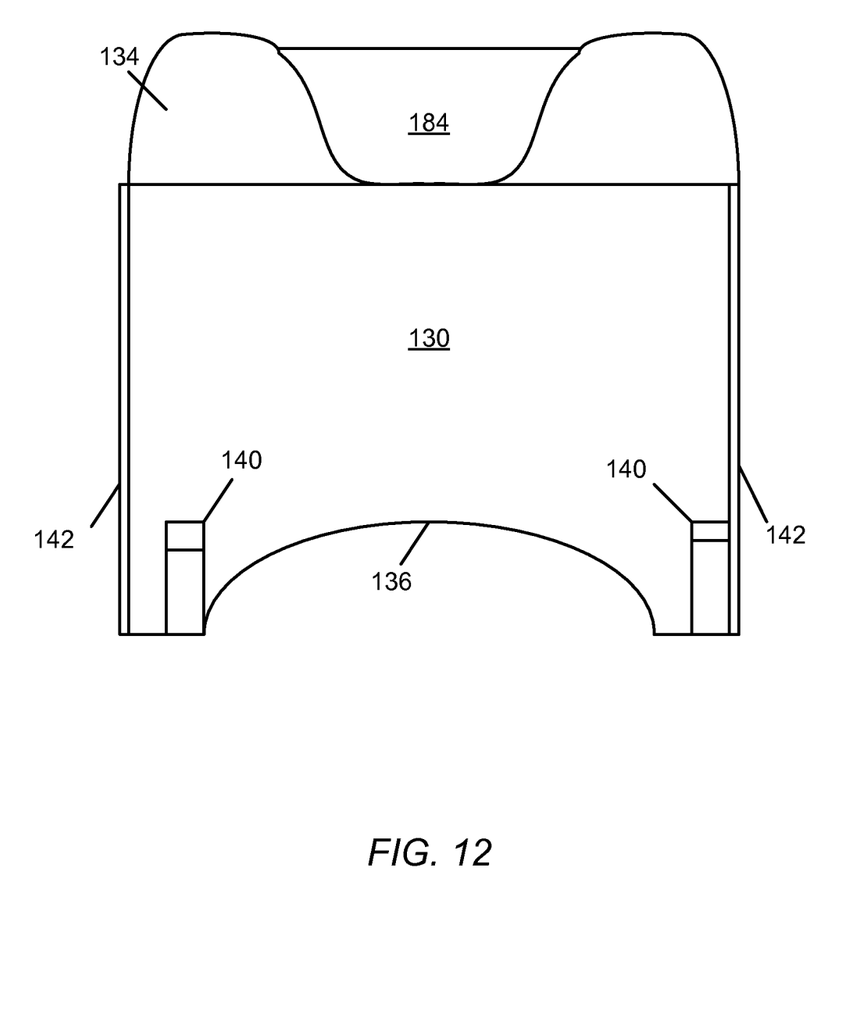
FIG. 12 is an elevated rear view of the drawer.

FIG. 12 is an elevated view of the drawer from the rear end of the drawer. The handle 134 has an indent 184 shaped to receive the person's forefinger. The tongues 142 are on opposite sides of the support surface 130. The posts 140 project from the rear edge of the support surface 130.

Figure 13:
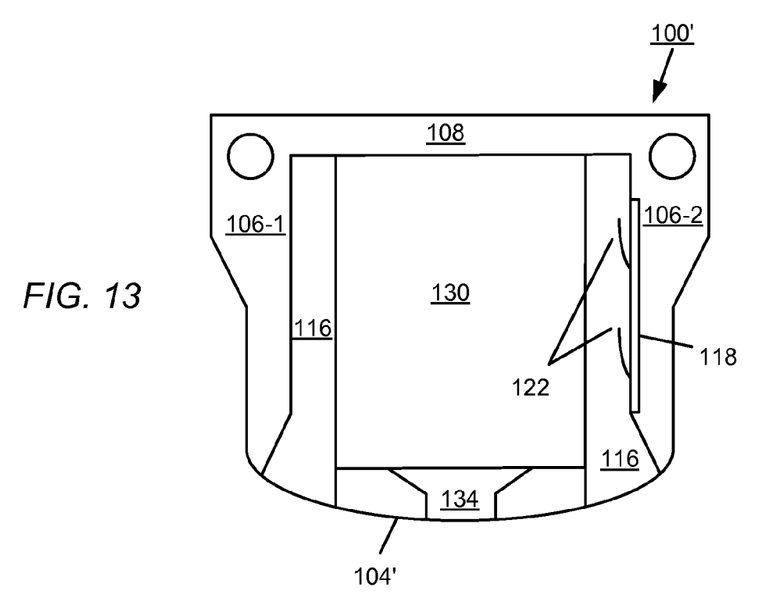
FIG. 13 is a top view of an embodiment of the sample tray having a single magnetically closing drawer.
Figure 14:
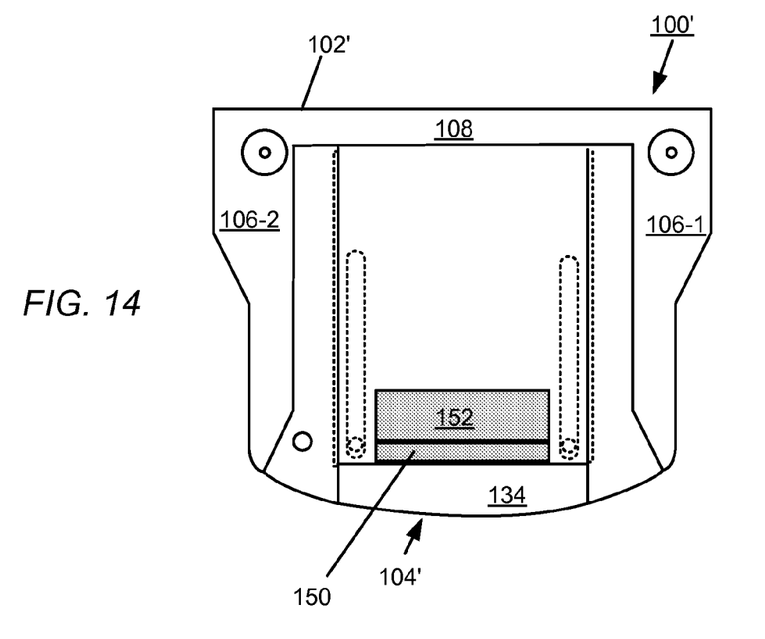
FIG. 14 is a bottom view of an embodiment of the sample tray having a single magnetically closing drawer.

FIG. 13 shows a top view and FIG. 14 shows a bottom view of another embodiment of a sample tray 100' with one compartment 120' and one magnetically closing drawer 104'. The sample tray 100' uses two magnets 150, 152 to close and secure the drawer 104' within the compartment 120'. Instead of coupled for rotary motion, like the sample tray 100 of FIG. 3, this sample tray 100' can be fixed within the sample chamber.

While the invention has been shown and described with reference to specific preferred embodiments, it should be understood by those skilled in the art that various changes in form and detail may be made therein without departing from the spirit and scope of the invention as defined by the following claims.

What is claimed is:

1. A sample tray for use in a sample manager of a liquid chromatography system, comprising:
    a base having opposing spaced-apart side walls separated by a cross wall that divides the base into two compartments, with one compartment on each side of the cross wall, the side walls and cross wall bounding each of the two compartments on three sides, with a fourth side of each compartment being open, each compartment being sized to closely receive a sample-vial carrier, each compartment having a surface with a magnet affixed to an underside of the surface at an edge of the open fourth side of that compartment; and
    a pair of drawers slidably coupled to the base, each drawer sliding into the open fourth side of one of the two compartments over the surface of that compartment, each drawer having a support surface for supporting a sample-vial carrier, the support surface having a top side and a bottom side, the support surface of each drawer having a magnet affixed on the bottom side, the magnet on the bottom side of the support surface of each drawer being in alignment with the magnet affixed to the underside of the surface of the compartment into which that drawer slides, the magnet of each drawer and the magnet of the compartment into which that drawer slides biasing that drawer into its compartment when the magnets are brought into proximity of each other.

2. The sample tray of claim 1, wherein one of the two side walls in each compartment has one or more leaf springs extending laterally thereof towards an interior region of the compartment in order to bias a sample-vial carrier disposed within the drawer, when closed, towards the other side wall.

3. The sample tray of claim 1, wherein the cross wall has a vertical hole for receiving a fastener by which to couple the sample tray to a drive mechanism underneath the sample tray, the vertical hole being located at a central point of the sample tray about which the sample tray turns when coupled to and rotated by the drive mechanism.

4. The sample tray of claim 1, wherein only one of the two compartments has a hole extending through for use in calibrating a position of the sample tray.

5. The sample tray of claim 1, wherein each compartment is approximately 5 inches in width and approximately 3.5 inches in depth.

6. The sample tray of claim 1, wherein each drawer has opposing side edges, and each side edge of the drawer has a tongue extending laterally from that side edge, and wherein each compartment has opposing side platforms, each platform having a side groove for slidably receiving the tongue at one of the side edges of the drawer.

7. The sample tray of claim 1, wherein each drawer has arching posts at a rear end of the drawer, for guiding a sample-vial carrier into position within the drawer.

8. A sample manager of a liquid chromatography system, comprising:
    a thermal chamber;
    a sample tray mounted within the thermal chamber, the sample tray comprising:
        a base having opposing spaced-apart side walls separated by a cross wall that divides the base into two compartments, with one compartment on each side of the cross wall, the side walls and cross wall bounding each of the two compartments on three sides, with a fourth side of each compartment being open, each compartment being sized to closely receive a sample-vial carrier, each compartment having a top surface and a bottom surface with a magnet affixed to the bottom surface at an edge of the open fourth side of that compartment; and
        a pair of drawers slidably coupled to the base, each drawer sliding into the open fourth side of one of the two compartments, each drawer having a support surface for supporting a sample-vial carrier, the support surface having a top side and a bottom side, the support surface of each drawer having a magnet affixed at an edge of the bottom side, the magnet at the edge of the bottom side of the support surface of each drawer being in alignment with the magnet affixed to the bottom surface of the compartment into which that drawer slides, the magnet of each drawer and the magnet of the compartment into which that drawer slides biasing that drawer into its compartment when the magnets are brought into proximity of each other.

9. The sample manager of claim 8, further comprising:
    a rotating drive mechanism disposed below the sample tray; and wherein the cross wall has a vertical hole for receiving a fastener by which to couple the sample tray to the rotating drive mechanism, the vertical hole being located at a central point of the sample tray about which the sample tray turns when rotated by the rotating drive mechanism.

10. The sample manager of claim 8, wherein the sample tray has one or more leaf springs extending laterally from one of the two side walls in each compartment towards an interior region of that compartment in order to bias a sample-vial carrier disposed within that drawer, when closed, towards the other side wall of that compartment.

11. A liquid chromatography system, comprising:
    a sample manager having a thermal chamber with a sample tray mounted therein, the sample tray comprising:
        a base having opposing spaced-apart side walls separated by a cross wall that divides the base into two compartments, with one compartment on each side of the cross wall, the side walls and cross wall bounding each of the two compartments on three sides, with a fourth side of each compartment being open, each compartment being sized to closely receive a sample-vial carrier, each compartment having a top surface and a bottom surface with a magnet affixed to the bottom surface at an edge of the open fourth side of that compartment; and
        a pair of drawers slidably coupled to the base, each drawer sliding into the open fourth side of one of the two compartments, each drawer having a support surface for supporting a sample-vial carrier, the support surface having a top side and a bottom side, the support surface of each drawer having a magnet affixed at an edge of the bottom side, the magnet at the edge of the bottom side of the support surface of each drawer being in alignment with the magnet affixed to the bottom surface of the compartment into which that drawer slides, the magnet of each drawer and the magnet of the compartment into which that drawer slides biasing that drawer into its compartment when the magnets are brought into proximity of each other.

12. The liquid chromatography system of claim 10, further comprising a rotating drive mechanism disposed below the sample tray; and wherein the cross wall has a vertical hole for receiving a fastener by which to couple the sample tray to the rotating drive mechanism, the vertical hole being located at a central point of the sample tray about which the sample tray turns when rotated by the rotating drive mechanism.

* * * * *